US007053125B2

(12) United States Patent
Lewis et al.

(10) Patent No.: US 7,053,125 B2
(45) Date of Patent: May 30, 2006

(54) CONTROLLED DISPERSION OF COLLOIDAL SUSPENSION BY COMB POLYMERS

(75) Inventors: Jennifer A. Lewis, Urbana, IL (US); Glen Kirby, Urbana, IL (US); Josephine Ho-Wah Cheung, Waltham, MA (US); Ara Avedis Jeknavorian, Chelmsford, MA (US)

(73) Assignees: The Board of Trustees of the University of Illinois, Urbana, IL (US); W.R. Grace & Co.-Conn., Columbia, MD (US)

( * ) Notice: Subject to any disclaimer, the term of this patent is extended or adjusted under 35 U.S.C. 154(b) by 350 days.

(21) Appl. No.: 10/336,636

(22) Filed: Jan. 3, 2003

(65) Prior Publication Data

US 2004/0096469 A1 May 20, 2004

Related U.S. Application Data

(60) Provisional application No. 60/426,297, filed on Nov. 14, 2002.

(51) Int. Cl.
*A61K 47/32* (2006.01)
*A61K 47/34* (2006.01)
*B01F 3/12* (2006.01)
*B01F 17/52* (2006.01)

(52) U.S. Cl. ............ 516/90; 514/772.1; 516/77; 516/78; 516/79; 516/87; 516/88; 516/92; 516/93; 516/95; 516/97; 524/504; 524/547; 524/548; 524/555; 524/560; 524/588; 524/599; 524/602

(58) Field of Classification Search ........... 516/77, 516/78, 79, 87, 88, 90, 92, 93, 95, 97
See application file for complete search history.

(56) References Cited

U.S. PATENT DOCUMENTS

| | | | |
|---|---|---|---|
| 4,426,356 A | 1/1984 | Nair | 419/21 |
| 4,471,100 A | 9/1984 | Tsubakimoto et al. | 525/367 |
| 4,946,904 A | 8/1990 | Akimoto et al. | 525/327.8 |
| 4,960,465 A | 10/1990 | Arfaei | 106/724 |
| 5,100,984 A | 3/1992 | Burge et al. | 526/240 |
| 5,237,017 A | 8/1993 | Akiyama et al. | 525/366 |
| 5,369,198 A | 11/1994 | Albrecht et al. | 526/240 |
| 5,393,343 A | 2/1995 | Darwin et al. | 106/808 |
| 5,416,071 A | 5/1995 | Igari et al. | 514/8 |
| 5,424,362 A | 6/1995 | Hwang et al. | 525/71 |
| 5,424,364 A | 6/1995 | Simms et al. | 525/170 |
| 5,424,466 A | 6/1995 | Stern et al. | 554/175 |
| 5,424,467 A | 6/1995 | Bam et al. | 554/216 |
| 5,424,477 A | 6/1995 | Higuchi et al. | 560/40 |
| 5,516,836 A | 5/1996 | Sauer et al. | 524/558 |
| 5,556,460 A | 9/1996 | Berke et al. | 106/823 |
| 5,597,871 A | 1/1997 | Auschra et al. | 525/309 |
| 5,643,247 A | 7/1997 | Fernandez et al. | 604/891.1 |
| 5,651,986 A | 7/1997 | Brem et al. | 424/484 |
| 5,654,006 A * | 8/1997 | Fernandez et al. | 424/489 |
| 5,665,158 A | 9/1997 | Darwin et al. | 106/808 |
| 5,753,037 A | 5/1998 | Drs et al. | 106/823 |
| 5,753,261 A | 5/1998 | Fernandez et al. | 424/450 |
| 5,811,124 A | 9/1998 | Fernandez et al. | 424/489 |
| 5,820,879 A | 10/1998 | Fernandez et al. | 424/450 |
| 5,883,196 A | 3/1999 | Rath et al. | 525/285 |
| 5,891,313 A | 4/1999 | Johnson et al. | 204/451 |
| 5,958,858 A | 9/1999 | Bettiol et al. | 510/351 |
| 6,008,181 A | 12/1999 | Cripe et al. | 510/426 |
| 6,015,781 A | 1/2000 | Vinson et al. | 510/302 |
| 6,020,303 A | 2/2000 | Cripe et al. | 510/503 |
| 6,051,636 A | 4/2000 | Johnson et al. | 524/98 |
| 6,060,443 A | 5/2000 | Cripe et al. | 510/426 |
| 6,093,856 A | 7/2000 | Cripe et al. | 568/625 |
| 6,107,409 A | 8/2000 | Hogan et al. | 525/285 |
| 6,127,094 A | 10/2000 | Victor et al. | 430/284.1 |
| 6,133,222 A | 10/2000 | Vinson et al. | 510/428 |
| 6,133,227 A | 10/2000 | Barnabas et al. | 510/530 |
| 6,136,333 A | 10/2000 | Cohn et al. | 424/423 |
| 6,136,769 A | 10/2000 | Asano | 510/329 |
| 6,139,623 A | 10/2000 | Darwin et al. | 106/823 |
| 6,150,459 A | 11/2000 | Mayes et al. | 525/54.1 |
| 6,153,577 A | 11/2000 | Cripe et al. | 510/356 |
| 6,207,749 B1 | 3/2001 | Mayes et al. | 524/731 |
| 6,211,249 B1 | 4/2001 | Cohn et al. | 514/772.1 |
| 6,228,829 B1 | 5/2001 | Vinson et al. | 510/357 |
| 6,242,406 B1 | 6/2001 | Katsuda et al. | 510/357 |
| 6,258,161 B1 | 7/2001 | Kerkar et al. | 106/808 |
| 6,277,191 B1 | 8/2001 | Budiansky et al. | 106/802 |

(Continued)

FOREIGN PATENT DOCUMENTS

AU  B-64095/80  9/1982

(Continued)

OTHER PUBLICATIONS

Chemical abstracts accession No. 2000:795091 for Sakai et al., "Influence of various types of inorganic salts on dispersion mechanisms of comb-type polymer containing grafted polyethylene oxide chains," Journal of the Ceramic Society of Japan, 2000.*

(Continued)

*Primary Examiner*—Robert Sellers
(74) *Attorney, Agent, or Firm*—Evan Law Group LLC

(57) ABSTRACT

Comb polymers are used as dispersants to increase the stability of colloidal suspensions containing multivalent or high concentrations of monovalent ions. Stabilized colloidal suspensions and methods of forming stabilized colloidal suspensions are described, including suspensions containing ceramic precursors or bioactive agents useful in forming ceramic substrates or pharmaceutical compositions, respectively.

40 Claims, 8 Drawing Sheets

U.S. PATENT DOCUMENTS

| | | | |
|---|---|---|---|
| 6,441,054 B1 * | 8/2002 | Ou et al. | 516/11 |
| 6,599,647 B1 * | 7/2003 | Oguri et al. | 428/703 |
| 6,670,415 B1 * | 12/2003 | Jardine et al. | 524/445 |
| 2002/0121229 A1 | 9/2002 | Jardine et al. | 106/681 |
| 2002/0147282 A1 | 10/2002 | Mayes et al. | 525/245 |
| 2002/0182171 A1 | 12/2002 | Detert et al. | 424/78.27 |
| 2003/0032727 A1 | 2/2003 | Narayan-Sarathy et al. | 525/100 |

FOREIGN PATENT DOCUMENTS

| | | |
|---|---|---|
| DE | 2052749 | 5/1972 |
| EP | 0 263 490 | 1/1995 |

OTHER PUBLICATIONS

Bell, Nelson, et al., "*Cation-Induced Collapse of Low-Molecular-Weight Polyacrylic Acid in the Dispersion of Barium Titanate*", Journal of Colloid and Interface Science 254, (2002), pp. 296-305.

Berg, J.M., et al., "*Interactions between Mica Surfaces in Sodium Polyacrylate Solutions Containing Calcium Ions*", Journal of Colloid and Interface Science, 161, (1993) pp. 182-189.

Breitenbach, A., et al. "*Branched biodegradable polyester for parenteral drug delivery systems*", Journal of Controlled Release, vol. 64, (2000) pp. 167-178.

Cesarano III, Joseph et al., "*Processing of Highly Concentrated Aqueous x-Alumina Suspensions Stablized with Polyelectrolytes*", J. Am. Ceram. Soc., vol. 71 No. 12, pp. 1062-1067, (1988).

Cesarano III, Joseph et al., "*Stability of Aqueous x-$Al_2O_3$ Suspensions with Poly(methacrylic acid) Polyelectrolyte*", J. Am. Ceramic Soc., vol. 7, No. 4, pp. 250-255 (1988).

Dahlgren, M., "*Effect of Counterion Valency and Ionic Strength on Polyelectorlyte Adsorption*", Langmuir vol. 10, No. 5, (1994), pp. 1580-1583.

De L. Costello, et al., "*Experimental investigations of the interaction forces in concentrated dispersions*", Colloids and Surfaces A: Physiochem. Eng. Aspects, 77, (1993), pp. 55-63.

Hadjichristidis, N., "*Polymers with Complex Architecture by Living Anionic Polymerization*", Chem. Rev. vol. 101, (2001) pp. 3747-3792.

Laarz, E. et al., "The Effect of Nionic Polyelectrolytes on the Properties of Aqueous Silicon Nitride Suspensions", J. of European Ceramic Society, vol. 20, pp. 431-440, (2000).

Li, C., et al., "*Effect of a comb-like amphiphilic polymer on the stability of alumina dispersions*", Colloids and Surfaces, 69, (1992), pp. 155-158.

Li, Chia-Chen, et al., "*Interaction between Dissolved Ba2+ and PAA-NH4 Dispersant in Aqueous Barium Titanate Suspensions*", Journal of the American Ceramic Society, vol. 85, No. 6, (2002), pp. 1449-1455.

Napper, Donald H., "*Polymeric Stabilization of Colloidal Dispersions*" Academic Press, Inc., (1983), pp. 28-30.

Orgeret-Ravanat, et al., "*Adsorption/Desorption of a PEO-rich Comb-like Polymer at a Silica/Aqueous Solution Interface*", Colloids and Surfaces vol. 33, (1988), pp. 109-119.

Reed, James S., "*Principles of Ceramic Processing*", $2^{nd}$, Ed., John Wiley & Sons, Inc. (1995), pp. 525-541.

Sakai, E., et al., "*Dispersion Mechanism of Comb-Type Superplasticizers Containing Grafted Poly(ethylene oxide) Chains*", Macromol. Symp. 175, (2001), pp. 367-376.

Schwartz, Steven A., "*Gypsum Dispersing Agents*", Londell Chemical Company, pp. 1-10, (2002).

Stenius, P. et al., "*Aggregation in concentrated kaolin suspensions stabilized by polyacrylate*", Colloids and Surfaces, vol. 51, (1990) pp. 219-238.

Tobori, N. et al., "*Rheological behavior of highly concentrated aqueous calcium carbonate suspensions in the presence of polyelectrolytes*", Colloids and Suraces A: Physiochem. Eng. Aspects 00, (2002), pp. 1-9.

Uhrig, D., et al., "*Synthesis of Combs, Centipedes, and Barbwires: Poly(isoprene-graft-styrene)Regular Multigraft Copolymers with Truifunctional, Tetrafunctional, and Hexafunctional Branch Points*", Maromolecules vol. 35, (2002), pp. 7182-7190.

Vermohlen, K., et al., "*Adsorption of polyelectrolytes onto oxides—the influence of ionic strength, molar mass, and Ca2+ ions*", Colloids and Surfaces A: Physicochem. Eng. Aspects 163 (2000, pp. 45-53.

ADVA® Flow Superplasticizer ASTM C494, Type F (carboxylated polyether) with Material Safety Data Sheet (MSDS), Grace Construction Products 10p., Nov. 13, 2002.

Axim Italcementi Group, Catexol™ Superflux 2000 PC, with Material Safety Data Sheet (MSDS), 7p., Nov. 13, 2002.

Polymer Source, Inc., Information Sheet—Custom Synthesis, comb polymer (poly(acrylic acid) backbone and poly(ethylene oxide) teeth), 2p., Nov. 13, 2002.

Silkroad C&T:Admixtures for Concrete, PEMA-200N, Product Information Sheet, 2p., Nov. 13, 2002.

Takemoto Oil & Fat Co. Ltd. Product Information Sheet, 2p., Nov. 13, 2002.

\* cited by examiner

Polyacrylic Acid (PAA)

Polyacrylic Acid with Polyethylene Oxide Cap (PAA-PEO)

CONTROLLED DISPERSION OF COLLOIDAL SUSPENSION BY COMB POLYMERS

REFERENCE TO RELATED APPLICATIONS

This application claims the benefit of U.S. Provisional Application No. 60/426,297, filed Nov. 14, 2002, entitled "Controlled Dispersion of Colloidal Suspensions by Comb Polymers," which is incorporated by reference.

BACKGROUND

Most any liquid that contains particles that are not fully solubilized can be characterized as a colloidal suspension. Colloidal suspensions enjoy widespread use in applications ranging from advanced materials to drug discovery. Colloid based products include paints, inks, coatings, ceramic precursors, cosmetics, and pharmaceutical compositions. In the case of ceramics, concentrated colloidal suspensions may be fabricated into dense components by sintering.

The viscosity of colloid suspensions can vary over a wide range from free-flowing liquid to flocculated gel. Dispersants that modify viscosity are often added to colloidal suspensions. A major benefit of viscosity control is the ability to lower the viscosity of a concentrated suspension. By lowering the viscosity, a suspension may be processed through pumps, pipes, and other machinery in a simpler and more cost effective manner. By tailoring interactions between colloidal particles through the addition of a dispersant, one can alter the viscosity of colloids to make them suitable for use in a broad array of applications. Through dispersant addition, colloidal suspensions may be processed at higher solids content than would otherwise be possible.

Polyacrylic acid (PAA) is the polyelectrolyte dispersant most widely used for the aqueous processing of ceramics. PAA contains carboxylic acid groups, one per monomer unit, along its backbone. By adding PAA, the dispersion of the colloidal particles is increased, thus reducing aggregation or flocculation. As flocculation is reduced, viscosity decreases. Another common dispersant used in ceramics processing is poly(methacrylic acid) (PMAA). PMAA contains carboxylic acid groups and methyl substituents on the backbone.

These polyelectrolyte dispersants are believed to reduce flocculation by stabilizing the colloid particles through the negative charge generated when the carboxylic acid functional groups are deprotonated. When deprotonated or ionized, the negatively charged carboxylic groups are believed to form an electrostatic repulsive barrier between the particles that form the colloid, thus reducing flocculation. It has also been postulated that the steric requirements of the dispersant provides additional stabilization.

PAA dispersant systems become less effective at reducing viscosity when higher ionic strength colloidal suspensions, especially those containing multivalent ions, are involved. It is believed that the multivalent ions interfere with the electrostatic repulsive barrier of the carboxylic groups. This may result in a decreased electrostatic repulsive barrier between the colloidal particles, thereby increasing flocculation. Hence, there is a need for dispersants that can reduce flocculation of suspended particles and thus provide lowered viscosity in high ionic strength colloidal suspensions.

BRIEF SUMMARY

In one aspect, a colloidal suspension includes particles, such as metals, ceramic precursors, semiconductors, polymers, biodegradable polymers, bioactive agents, and mixtures thereof; a comb polymer; and multivalent ions having a suspension concentration of at least 0.001 M.

In another aspect, a colloidal suspension includes particles, such as metals, ceramic precursors, semiconductors, polymers, biodegradable polymers, bioactive agents, and mixtures thereof; a comb polymer; and monovalent ions having a suspension concentration of at least 0.1 M.

In another aspect, a colloidal suspension includes hydroxyapatite particles, titanium oxide particles, lead zirconate particles, titanate particles, alumina particles, silica particles, zirconia particles, silicon nitride particles, barium titanate particles, silicon carbide particles, or mixtures of these particles; a comb polymer; and multivalent ions having a suspension concentration of at least 0.001 M.

In another aspect, a colloidal suspension can include hydroxyapatite particles, titanium oxide particles, lead zirconate particles, titanate particles, alumina particles, silica particles, zirconia particles, silicon nitride particles, barium titanate particles, silicon carbide particles, or mixtures of these particles; a comb polymer; and monovalent ions having a suspension concentration of at least 0.1 M.

In another aspect, a method of forming a mixture is provided where the mixture includes a comb polymer; a carrier liquid; particles, such as metals, ceramic precursors, semiconductors, polymers, biodegradable polymers, bioactive agents, and mixtures thereof; and multivalent ions having a suspension concentration of at least 0.001 M.

In another aspect, a method of forming a mixture is provided where the mixture includes a comb polymer; a carrier liquid; particles, such as metals, ceramic precursors, semiconductors, polymers, biodegradable polymers, bioactive agents, and mixtures thereof; and monovalent ions having a suspension concentration of at least 0.1 M.

In another aspect, a method of forming a colloidal suspension is provided where a comb polymer is mixed with a mixture that includes a carrier liquid; hydroxyapatite particles, titanium oxide particles, lead zirconate particles, titanate particles, alumina particles, silica particles, zirconia particles, silicon nitride particles, barium titanate particles, or silicon carbide particles; or mixtures of these particles; and multivalent ions having a suspension concentration of at least 0.001 M.

In another aspect, a method of forming a colloidal suspension is provided where a comb polymer is mixed with a mixture that includes a carrier liquid; hydroxyapatite particles, titanium oxide particles, lead zirconate particles, titanate particles, alumina particles, silica particles, zirconia particles, silicon nitride particles, barium titanate particles, silicon or carbide particles; or mixtures of these particles; and monovalent ions having a suspension concentration of at least 0.1 M.

In another aspect, a method of making a ceramic substrate is provided that includes solidifying a colloidal suspension to form a substrate where the colloidal suspension includes a carrier liquid, ceramic precursor particles, a comb polymer, and multivalent ions having a suspension concentration of at least 0.001 M.

In another aspect, a method of making a ceramic substrate is provided that includes solidifying a colloidal suspension to form a substrate where the colloidal suspension includes a carrier liquid, ceramic precursor particles, a comb polymer, and monovalent ions having a suspension concentration of at least 0.1 M.

In another aspect, a method of lowering the viscosity of a colloidal suspension includes adding a comb polymer to a mixture that includes multivalent ions having a suspension concentration of at least 0.001 M.

In another aspect, a method of lowering the viscosity of a colloidal suspension includes adding a comb polymer to a mixture that includes monovalent ions having a suspension concentration of at least 0.1 M.

The scope of the present invention is defined solely by the appended claims, and is not affected to any degree by the statements within this summary.

DETAILED DESCRIPTION

Figure 1:
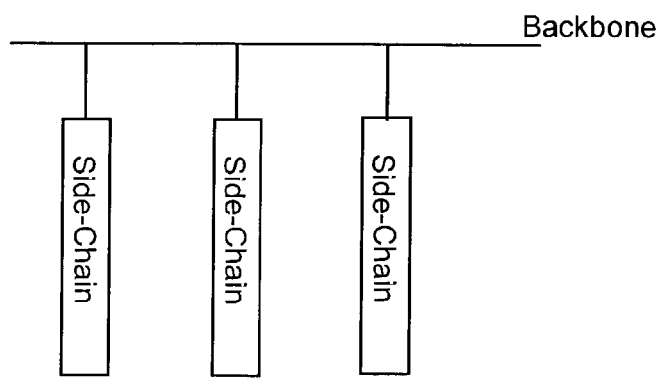
FIG. 1 shows an illustrative example of a comb polymer.

The present invention includes suspensions stabilized by comb polymer dispersants and methods of using comb polymer dispersants to regulate the stability of colloidal suspensions having a high ionic strength, including suspensions containing multivalent ions. In relation to polymers having only ionizable side-chains, the comb polymers of the present invention markedly reduce the viscosity of high ionic strength suspensions. By modifying the structure of the comb polymer, its concentration in the colloidal suspension, and the properties of the carrier liquid, the viscosity of the suspension may be altered by several orders of magnitude.

Colloidal Suspensions

Colloidal particles have a substantial fraction of their atoms or molecules at the surface. When placed in a carrier liquid, an interface exists between the surface of the particles and the carrier liquid. The behavior of the resultant colloid, including stability, digestibility, film forming properties, and viscous and elastic properties, is chiefly determined by how this surrounding interface interacts with the surface of the colloidal particles and the carrier liquid.

Solutions, unlike colloidal dispersions or suspensions, lack an identifiable interface between their solubilized molecules and the solvent. In solutions, the solubilized molecules are in direct contact with the solvent, while in colloidal suspensions only the surface of the microparticles are in direct contact with the carrier liquid. Hence, the carrier liquid does not solubilize the particles that make up a colloid; instead, the carrier liquid "carries" the particles. By carrying the particles, a suspension or dispersion results. The terms suspension and dispersion are used interchangeably.

The interfaces between the suspended colloidal particles, and the carrier liquid or liquid mixture in which they reside, play the dominant role in determining the behavior and capabilities of the colloidal dispersion. Colloidal suspensions are considered stable if the particles that form the colloid are separated or deflocculated, i.e., not aggregated or flocculated. In relation to colloidal suspensions, stability is the ability of the suspension to resist change, such as aggregation, over time.

Long-range attractive forces, such as van der Waals forces, are believed to pull colloidal particles together. When colloidal particles are pulled together, the colloidal dispersion or suspension is destabilized. This destabilization is often referred to as aggregation or flocculation and can result in precipitation of the aggregated particles from the colloidal suspension. Additionally, as the suspension flocculates its viscosity increases.

As colloidal suspensions flocculate, they can go from a liquid phase to a gel phase. Thus, as suspension stability is reduced, the liquid becomes a gel. There is no specific point at which a liquid becomes a gel. In general, however, liquids freely flow while gels do not. A liquid will conform to the shape of a container in which it is placed, while a gel can have a physical form separate from the container where it resides.

Alternatively, columbic, steric, and other repulsive interactions are believed to repel colloidal particles from each other. If the particles cannot aggregate together, the stability of the colloidal suspension is increased and flocculation may be reduced. Thus, through the reduction of flocculation, a suspension's viscosity may be decreased.

In the past it was believed that comb polymers having nonionizable side-chains, in addition to ionizable side-chains, provided no practical benefit over commonly used dispersants having only ionizable side-chains, such as polyacrylic and polymethacrylic acid, in the stabilization of colloidal suspensions. It was also believed that varying the length (molecular weight) of the nonionizable side-chains had no appreciable effect on the ability of the comb polymer to stabilize colloidal suspensions. This position is supported in Bergstrom et al., *The effect of anionic polyelectrolytes on the properties of aqueous silicon nitride suspensions*, Journal of the European Ceramic Society 20 (2000) 431–440.

Surprisingly, the present invention provides embodiments that can significantly reduce the tendency of colloidal particles to flocculate in relation to dispersants having only ionizable side-chains through the use of comb polymer dispersants having nonionizable, in addition to ionizable, side-chains. The results are especially beneficial when the colloidal suspensions have high ionic strength arising from multivalent ions, and/or high concentrations of monovalent ions.

While not wishing to be bound by any particular theory, it is believed that the nonionizable side-chains of the comb polymers "shield" the ionized side-chains from ion bridging interactions (where an ion attracts dispersant coated particles), especially from multivalent ions. The nonionizable side-chains are also believed to impart steric stabilization over an interparticle separation distance that increases with the molecular weight of the nonionizable side-chains, thus making the suspension less sensitive to changes in ionic strength. In this manner, the comb polymers are believed to maintain repulsive forces between the suspended particles, even in the presence of the multivalent ions.

One possible explanation regarding how the comb polymers increase the repulsive forces between the suspended particles is that the like-charged comb polymers attach to the particles and congregate about the ions, thus forming a "protective shield." The repulsive forces generated by the adsorbed comb polymers are believed to reduce the tendency of the particles to aggregate, thus counteracting the attractive van der Waals forces. The charge carried by the comb polymers may be positive or negative; however, the net charge of the comb polymers adsorbed on the colloidal particle surfaces may be positive, negative, or neutral.

Carrier liquid

A feature of the present approach to colloidal viscosity control is that comb polymer dispersants are used to modify the suspension. Another consideration is the polarity of the carrier liquid in which the particles are suspended. The colloidal dispersions of the present embodiments contain particles that are not solubilized; instead, the particles are suspended in a carrier liquid. Depending on the comb polymer dispersant used, varying degrees of carrier liquid polarity may be used to further tune suspension viscosity. Mixtures of polar liquids and less-polar, or even non-polar liquids can be used to fine tune the polarity of the liquid carrier.

While many polar carrier liquids may be used to form the colloid dispersions, water is especially preferred at present. Other presently preferred carrier liquids that are less polar than water include alcohols, such as methanol, propanol, ethanol, and t-butanol, N,N-dimethylformamide (DMF), dimethyl sulfoxide (DMSO), acetone, acetonitrile, acetic acid, hexamethylphosphoric triamide (HMPA), tetrahydrofuran (THF), N,N-dimethylacetamide, N-methyl-2-pyrrolidone, tetramethyl urea, glycerol, ethylene glycol, or mixtures thereof.

Stabilized Against Flocculation

The stability of a colloidal suspension is defined as its ability to resist flocculation. The greater the number of particles that can be added to a given volume of carrier liquid without flocculation, the greater the stability of the suspension.

A colloidal suspension is stabilized against flocculation when at least 90% of the particles can be observed as being individual, rather than aggregated in groups of two or more. This determination is made by diluting a sample of the colloidal suspension to 1 part-per-million solids, placing the sample on a slide, and observing the sample by light microscopy.

Particles

The particles are suspended or dispersed in a carrier liquid to form a colloidal suspension. Preferable particles include metals, ceramic precursors, semiconductors, polymers, biodegradable polymers, bioactive agents, proteins, liposomes, and other biomolecules, or mixtures thereof. Preferably, the particles do not include calcium silicate hydrates, cement, cement precursors, calcium sulfate hemihydrates, gypsum, and gypsum precursors.

Examples of preferred metal particles for use in colloidal suspensions include elemental metal particles; such as iron, tin, zinc, aluminum, beryllium, niobium, copper, tungsten, silver, gold, molybdenum, platinum, cobalt, nickel, manganese, cerium, silicon, titanium, tantalum, and magnesium mixtures and alloys thereof; metal alloys such as steels and tool steels, stainless steels, plain carbon steels, low carbon steels, aluminum-nickel, brass, bronze; and alloys used for biomedical applications such as cobalt-chromium, cobalt-chromium-molybdenum, cobalt-chromium-tungsten-nickel, cobalt-nickel-chromium-molybdenum-titanium, and titanium-aluminum-vanadium alloys.

More preferable metal particles are selected from the group consisting of tool steels, molybdenum, nickel, gold, silver, platinum, titanium-aluminum-vanadium alloys, tungsten, and aluminum, or mixtures or alloys thereof. Especially preferable metal particles are selected from the group consisting of tool steels, molybdenum, and nickel, or mixtures thereof.

Ceramic precursor particles are those that can form ceramic substrates or materials when solidified. Examples of ceramic precursor particles include oxides, such as alumina, silica, zirconia, magnesium oxide, zinc oxide, tin oxide, titanium oxide, indium oxide, lanthanum oxide, yttrium oxide, calcium oxide, silver oxide, and iron oxide; clays and whitewares, such as kaolinite, bentonite, and feldspars; carbides, such as silicon carbide, boron carbide, and tungsten carbide; nitrides such as silicon nitride, aluminum nitride, and boron nitride; titanates, such as barium titanate, lead zirconate titanate, and lead zirconate strontium titanate; ferrites, such as zinc ferrite, manganese ferrite, iron ferrite, cobalt ferrite, nickel ferrite, copper ferrite, magnesium ferrite; manganites, such as manganese manganite and magnesium manganite; hydroxyapatite; calcium phosphate-based ceramics; diamond; and carbon black; and mixtures thereof. As previously stated, these precursors exclude calcium silicate hydrates, cement, cement precursors, calcium sulfate hemihydrates, gypsum, and gypsum precursors.

More preferable ceramic precursor particles are selected from the group consisting of hydroxyapatite, titanium oxide, lead zirconate, titanate, alumina, silica, zirconia, silicon nitride, barium titanate, and silicon carbide, or mixtures thereof. Especially preferable ceramic precursor particles are selected from the group consisting of hydroxyapatite, titanium oxide, barium titanate, and lead zirconate titanate, or mixtures thereof.

Preferable semiconductor particles are those that can form semiconducting materials when fully or partially solidified. Examples of semiconductor particles include silicon; silicon carbide; III—V semiconducting materials including gallium arsenide, gallium nitride, gallium phosphide, gallium antimide, aluminum antimide, indium arsenide, indium phosphide, and indium antimide; II–VI semiconducting materials including zinc oxide, cadmium sulfide, cadmium telluride, zinc sulfide, cadmium selenide, zinc selenide; and IV–VI semiconducting materials including lead sulfide and lead telluride; and mixtures thereof.

More preferable semiconductor particles are selected from the group consisting of gallium arsenide, indium arsenide, indium phosphide, silicon, cadmium sulfide, zinc sulfide, cadmium telluride, cadmium selenide, and zinc selenide, or mixtures thereof. Especially preferable semiconductor particles are selected from the group consisting of gallium arsenide, indium arsenide, and indium phosphide, or mixtures thereof.

Preferable polymer particles include, polystyrene, polyorganosiloxane, poly(methyl methacrylate), polystyrene, polylactic acids, acrylic latexes, polyorganosiloxane, cellulose, polyethylene, poly(vinyl chloride), poly(ethyl methacrylate), poly(tetrafluoroethylene), poly(4-iodostyrene/divinylbenzene), poly(4-vinylpyridine/divinylbenzene), poly (styrene/divinyl benzene), crosslinked melamine particles, phenolic polymer colloids, polyamide 6/6, natural rubber, and collagen, or mixtures thereof.

More preferable polymer particles are selected from the group consisting of acrylic latexes, poly(ethyl methacrylate), cellulose polystyrene, poly(methyl methacrylate), poly (lactic acids), natural rubber, polyethylene, and poly(vinyl chloride), or mixtures thereof. Especially preferable polymer particles are selected from the group consisting of acrylic latexes, poly(ethyl methacrylate), and cellulose, or mixtures thereof.

Preferable particles may also be bioactive agents. Many bioactive agents, including proteins, form multivalent ions. Thus, the current embodiments can stabilize suspensions containing multivalent and monovalent bioactive agents in addition to inorganic ions or counterions.

Bioactive agents, which may be delivered by colloidal suspensions, include drugs that act on the peripheral nerves, adrenergic receptors, cholinergic receptors, the skeletal muscles, the cardiovascular system, smooth muscles, the blood circulatory system, synoptic sites, neuroeffector junction sites, endocrine and hormone systems, the immunological system, the reproductive system, the skeletal system, autacoid systems, the alimentary and excretory systems, the histamine system, and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by colloidal suspensions include, but are not limited to, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, bone morphogenic proteins, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons such as interferon alpha-2a, interferon alpha-2b, and consensus interferon, interleukins, growth hormones such as human growth hormone and its derivatives such as methione-human growth hormone and des-phenylalanine human growth hormone, bovine growth hormone and porcine growth hormone, fertility inhibitors such as the prostaglandins, fertility promoters, growth factors such as insulin-like growth factor, coagulation factors, human pancreas hormone releasing factor, analogs and derivatives of these compounds, and pharmaceutically acceptable salts of these compounds, or their analogs or derivatives.

Other bioactive agents, which may be delivered by colloidal suspensions, include chemotherapeutic agents, such as carboplatin, cisplatin, paclitaxel, BCNU, vincristine, camptothecin, etopside, cytokines, ribozymes, interferons, oligonucleotides and oligonucleotide sequences that inhibit translation or transcription of tumor genes, functional derivatives of the foregoing, and generally known chemotherapeutic agents such as those described in U.S. Pat. No. 5,651,986.

Not only can many of these bioactive agents, including proteins, directly serve as the particles in a colloidal suspension, but they can also be mixed with biodegradable compositions or polymers to form particles. By grinding a mixture containing one or more biodegradable composition and bioactive agent into particles, colloidal suspensions may be formed. Many useful biodegradable compositions suitable for use with bioactive agents may be found in U.S. Pat. No. 5,416,071.

Examples of useful biodegradable polymers for use in particle formation include polyesters, such as poly(caprolactone), poly(glycolic acid), poly(lactic acid), and poly (hydroxybutryate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof. Examples of methods for forming particles from mixtures containing bioactive agents and biodegradable polymers are described in EPO 0 263 490.

More preferred bioactive agents are selected from the group consisting of drugs, proteins, enzymes, polynucleotides, lipoproteins, liposomes, polypeptides, chemotherapeutic agents, hormones, polysaccharides, steroids, analgesics, local anesthetics, antibiotic agents, anti-inflammatory corticosteroids, and mixtures thereof. Of course, calcium silicate hydrates, cement, cement precursors, calcium sulfate hemihydrates, gypsum, and gypsum precursors are not suitable bioactive agents.

Depending on their surface structure and the nature of the carrier liquid, the average effective diameter of particles suitable for colloid formation can vary over a wide range. By "average effective diameter" it is meant the longest dimension of the particle. Thus, if a particle is 0.01 μm in one dimension and 10 μm in another, the effective diameter of the particle is 10 μm.

Preferred particles have average effective diameters of 1 nanometer to 100 microns, more preferably 10 nanometers to 50 microns, and most preferably 20 nanometers to 3 microns.

Comb Polymer

Monomer units are the individual moieties that are repeated to form polymers. Multiple monomer units are covalently attached when in the form of a backbone of a polymer. Polymers that are made from at least two different monomer units are referred to as copolymers. Polymerizing or copolymerizing describes the process by which multiple monomers (i.e. chemical compounds) are reacted to form covalently linked monomer units that form polymers or copolymers, respectively. A discussion of polymers, monomer units, and the monomers from which they are made may be found in Stevens, *Polymer Chemistry: An Introduction*, $3^{rd}$ ed., Oxford University Press, 1999.

Comb polymers are polymers that have backbones to which side-chains are attached. A discussion of comb polymers and their various structures may be found in D. H. Napper, *Polymeric Stabilization of Colloidal Dispersions*, Academic Press, 1983 (pp. 28–30). An illustrative example of a comb polymer is depicted in FIG. 1.

The comb polymers of the current invention contain at least two types of side-chains and preferably are water-soluble. By water-soluble it is meant that at least one gram of the polymer may be solubilized in one Liter of the carrier liquid. Preferably, the first type of side-chain, referred to as ionizable, has moieties that ionize at the pH of the colloidal suspension. These moieties can ionize to either cationic or anionic states when they dissociate in the carrier liquid. If desired, comb polymers that form both cationic and anionic moieties upon dissociation may be combined to alter the stability of the colloidal suspension. Preferably, the second type of side-chain, referred to as nonionizable, does not ionize at the pH of the colloidal suspension.

Figure 2:
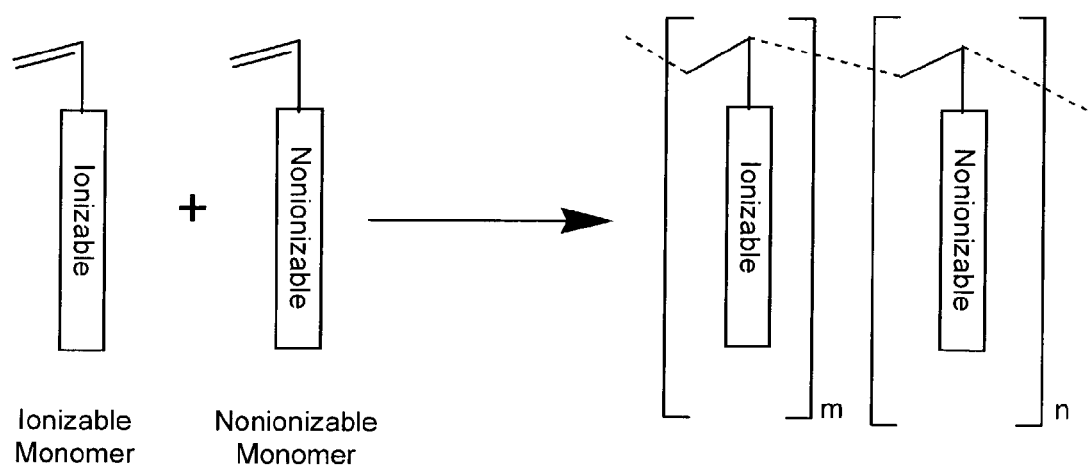
FIG. 2 shows an illustrative example of forming a comb polymer having nonionizable and ionizable side-chains provided by different monomers.

Although many variations to synthesize comb polymers are known, there are two basic pathways. The first is to form a copolymer from a monomer or monomer unit having ionizable side-chains and a monomer or monomer unit having nonionizable side-chains. An illustrative example of this synthesis pathway is shown in FIG. 2.

By varying the ratio of ionizable (m) to nonionizable (n) monomers combined to form the polymer, the resultant comb polymer may be tuned to stabilize a specific colloidal suspension, or group of suspensions. By maintaining a sufficient number of ionizable (hydrophilic) side-chains, in relation to nonionizable side-chains, the water solubility of the comb polymer may be maintained.

Figure 3:
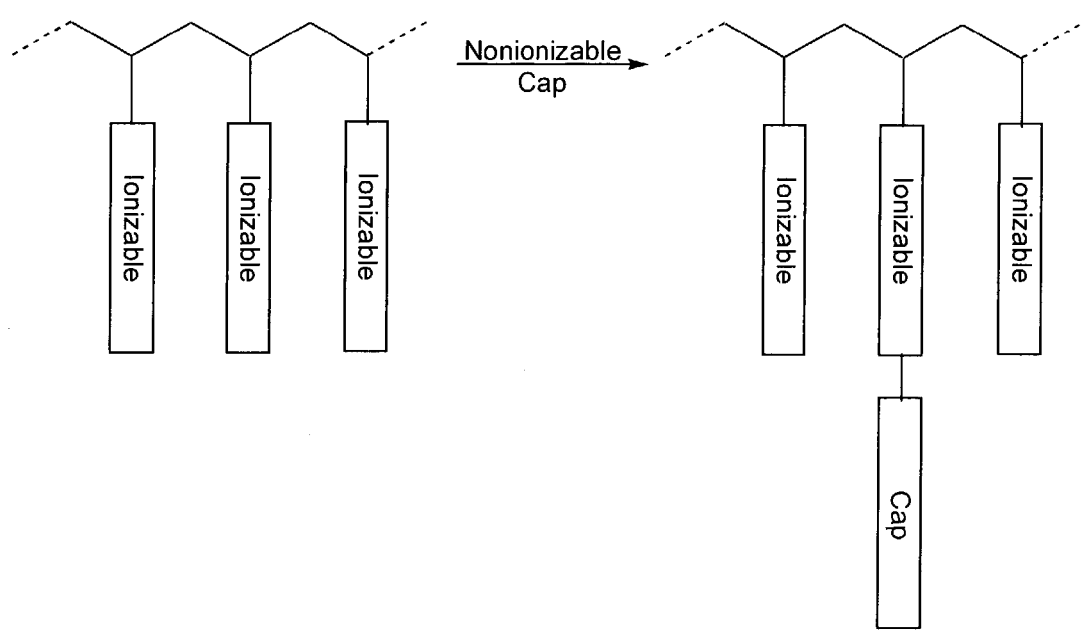
FIG. 3 shows an illustrative example of forming a comb polymer having nonionizable and ionizable side-chains provided by capping ionizable side-chains.

The second general comb polymer synthesis method begins with a polymer having ionizable groups on the backbone that can be functionalized with nonionizable groups (cap). By capping a portion of the polymer's ionizable groups with nonionizable groups, a comb polymer having both ionizable and nonionizable side-chains may be formed. An illustrative example of this synthesis pathway is shown in FIG. 3.

By controlling the reaction of the capping agent with the polymer, the number of ionizable side-chains that are converted to capped nonionizable side-chains may be varied. Thus, the resultant comb polymer may be tuned to stabilize a specific colloidal suspension, or group of suspensions. As above, water-solubility can be maintained by limiting the degree of capping of the hydrophilic backbone.

While any comb polymer may be used which provides the desired stability to the suspension, preferred comb polymers contain backbones including anionic or cationic polyelectrolytes. Examples of useful anionic polyelectrolytes include polymers containing carboxylic acid moieties, such as poly (acrylic acid), poly(methacrylic acid), poly(methyl methacrylate), poly(lauryl methacrylate), salts of carboxymethyl ether, carboxyl terminated poly(butadiene/acrylonitrile), poly(butadiene/maleic acid), poly(butyl acrylate/acrylic acid), poly(ethylene glycol) monocarboxymethyl ether monomethyl ether, poly(ethylene/maleic acid), poly(maleic acid), poly(methyl methacrylate/methacrylic acid), poly(vinyl methyl ether/maleic acid), poly(vinyl methyl ether/ monobutyl maleate), poly(vinly methyl ether/monoethyl maleate), poly(vinyl methyl ether/mono-iso-propyl maleate); polymers functionalized with sulfonic acid groups, such as poly(vinylsulfonic acid), poly(styrenesulfonic acid), poly(1,6)alpha-d-glucose sulfate; polymers functionalized with phosphoric acid groups, such as poly(vinylphosphoric acid) and poly(styrenephosphoric acid); polymers functionalized with phosphonic acid groups, such as poly(vinyl phosphonic acid) and poly(styrenephosphonic acid); and polymers functionalized with siloxane groups, such as poly (dimethylsiloxane); and mixtures thereof. Polymers suitable for backbone formation may be obtained from multiple chemical suppliers, including Polysciences, Inc., Warrington, Pa. and Sigma-Aldrich, Milwaukee, Wis.

More preferable anionic polyelectrolytes are selected from the group consisting of sulfonated naphthalene formaldehyde, sulfonated melamine formaldehyde, poly(vinyl phosphonic acid, poly(acrylic acid), poly(methacrylic acid), poly(vinylsulfonic acid), poly(vinylphosphoric acid), poly (styrene sulfonic acid), and poly(maleic acid), or mixtures thereof. Especially preferable anionic polyelectrolytes are selected from the group consisting of sulfonated naphthalene formaldehyde, sulfonated melamine formaldehyde, and poly (vinyl phosphonic acid, or mixtures thereof.

Examples of useful cationic polyelectrolytes include polymers containing amine moieties, such as poly(d-glucosamine), poly(acrylamide/2-methacryloxyethyltrimethylammonium bromide 80:20), poly(allylamine hydrochloride), poly(4-aminostyrene), poly(3-chloro-2-hydroxypropyl-2-methacroxyethyldimethylammonium chloride), poly(diallyldimethylammonium chloride), poly (2-dimethylaminoethyl methacrylate), polyethylenimine, poly(2-hydroxy-3-methacryloxypropyltrimethyl-ammonium chloride), poly(2-methacryloxyethyltrimethylammonium bromide), poly(N-methylvinylamine), poly(tetramethylene oxide) bis-4-aminobenzoate, poly(vinylamine) hydrochloride, poly(4-vinylbenzyltrimethylammonium chloride), poly(2-vinyl-1 methylpyridinium bromide), poly (4-vinyl-1 methylpyridinium bromide), poly(2-vinylpyridine), poly(4-vinylpyridine), poly(2-vinylpyridine N-oxide), poly(4-vinylpyridine N-oxide), and poly(N-vinylpyrrolidone/2-dimethylaminoethyl methacrylate) dimethyl sulfate quaternary, and mixtures thereof.

More preferable cationic polyelectrolytes are selected from the group consisting of poly(2-vinylpyridine N-oxide), poly(4-vinylpyridine N-oxide), poly(4-aminostyrene), poly (ethylene imine), poly(4-vinylpyridine), poly(2-vinylpyridine), poly(N-methylvinylamine), poly(d-glucosamine), and poly(vinyl imine) hydrochloride, or mixtures thereof. Especially preferable cationic polyelectrolytes are selected from the group consisting of poly(2-vinylpyridine N-oxide), poly (4-vinylpyridine N-oxide), and poly(4-aminostyrene), or mixtures thereof.

Examples of useful bio-compatible polymer backbones include, carboxyl terminated poly(azelaic anhydride), polycaprolactone, polycaprolactone diol, poly(glycolic acid), poly(dl-lactic acid), poly(l-lactic acid), poly(dl-lactide/glycolide), and poly(l-lactide/glycolide).

More preferable bio-compatible polymer backbones are selected from the group consisting of polyamines, polyamides, polyesteramides, poly(lactic acid), poly(glycolic acid), nucleic acids (DNA and RNA), proteins, polysaccharides, and poly(caprolactone), or mixtures thereof. Especially preferable bio-compatible polymer backbones are selected from the group consisting of polyamines, polyamides, and polyesteramides, or mixtures thereof.

Examples of useful capping agents for forming the neutral side-chains include polyethylene oxide, poly(ethylene glycol), poly(ethylene glycol) dimethyl ether, poly(ethylene glycol) monomethyl ether, polypropylene oxide, poly(propylene glycol), poly(methyl methacrylate), poly(vinyl alcohol), poly(vinyl pyrrolidone), poly(vinyl acetate), polyacrylamide, poly(oxyethylene), poly(vinyl methyl ether), and poly(dimethylsiloxane), or mixtures thereof. Suitable capping agents may be obtained from multiple chemical suppliers, including Polysciences, Inc., Warrington, Pa. and Sigma-Aldrich, Milwaukee, Wis.

More preferable capping agents include poly(vinyl alcohol), poly(vinyl acetate), poly(dimethylsiloxane), poly(ethylene oxide), poly(ethylene glycol), poly(propylene oxide), polyacrylamide, poly(vinyl pyrrolidone), and poly(oxyethylene), or mixtures thereof. Especially preferable capping agents include poly(vinyl alcohol), poly(vinyl acetate), and poly(dimethylsiloxane), or mixtures thereof.

Figure 4:
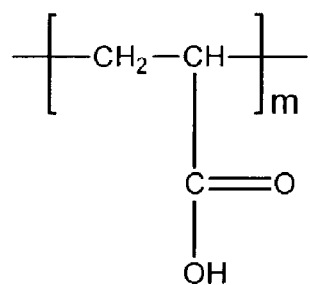
FIG. 4 shows polyacrylic acid (PAA) and a polyacrylic acid derivatized with nonionizable PEO side-chains to give a PAA-PEO comb polymer.
Figure 4:
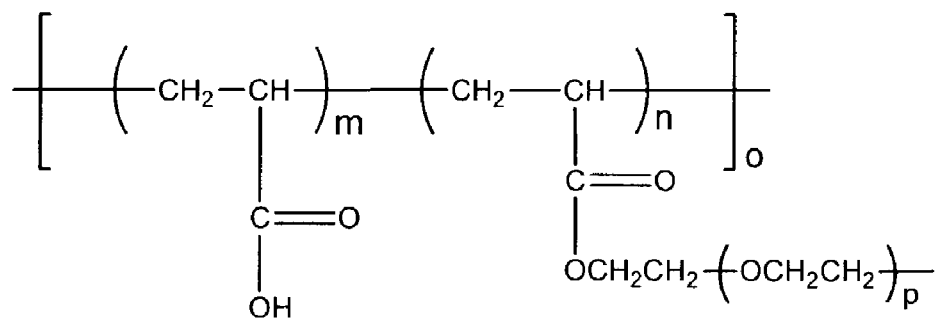

Especially preferred are comb polymers made from the reaction of a hydrophilic polyacrylic acid backbone with polyethylene oxide caps that results in a comb polymer having ionizable side-chains incorporating a carboxylic acid moiety and nonionizable side-chains incorporating a polyethylene oxide moiety. Referring to FIG. 4, polyacrylic acid is capped with polyethylene oxide. By varying m, n, and/or o the molecular weight of the comb polymer and the ratio of ionizable versus nonionizable side-chains may be altered. By varying p, the molecular weight of the cap may be altered. As used in this specification and appended claims, the term "a comb polymer" includes one or more polymeric units and one or more types of polymeric units.

In addition to changing the atomic structure of the backbone and side-chains, and the ratio between ionizable and nonionizable side-chains (m versus n), the molecular weight of the backbone (determined by o) and side-chains (determined by p) may be varied to control suspension stability. Preferable ratios of ionizable to nonionizable side-chains (m versus n) are from 20:1 to 1:1 and more preferably from 10:1 to 2:1. Preferable average molecular weights (grams/mole) of the comb polymer backbone (o) are from 1,000 to 15,000 and more preferably from 2,000 to 10,000. When polyacrylic acid backbones are used, preferable values for p result in polyethylene oxide caps having average molecular weights (grams/mole) from 100 to 5,000, more preferably from 600 to 3,000, and most preferably from 900 to 2,200.

High Ionic Strength Suspensions

The present invention is especially useful to stabilize high ionic strength colloidal suspensions. High ionic strength suspensions typically result from two sets of circumstances. The first are colloidal suspensions that contain high concentrations of monovalent ions solvated in the carrier liquid. Monovalent ions are those that attain a $^+1$ or $^-1$ ionization state when ionized in the carrier liquid. High concentration is preferably defined as a molarity of 0.1 or greater. More preferably the molarity is 0.5 or greater, and most preferably the molarity is 1.0 or greater.

A second circumstance resulting in high ionic strength involves colloidal suspensions that contain multivalent ions solvated at a molarity of 0.001 or greater in the carrier liquid. Preferably, the suspension contains multivalent ions at a molarity of 0.01 or greater, more preferably the suspension contains multivalent ions at a molarity of 0.1 or greater. Multivalent ions are those that attain a $^+2$ or higher, or a $^-2$ or lower, ionization state when ionized (solvated) in the carrier liquid.

The ionization state of an ion is determined by the charge it adopts in the carrier liquid. Depending on the atomic make-up of the ion, ions may be present in the $^+1$, $^-1$, $^+2$, $^-2$ or higher and lower ionization states ($^+3$ or $^+4$, for example).

Examples of monovalent cations are ionized alkali metals such as sodium and potassium, and multi-atom ions, including ammonium. Examples of monovalent anions are halides, including bromide and chloride, and multi-atom ions, including acetate, nitrite, and hypochlorite. Especially preferred monovalent ions include, ionized alkali earth metals, $NH_4^+$, $NO_3^-$, $ClO_3^-$, $IO_3^-$, and mixtures thereof.

Preferred monovalent cations include, but are not limited to ammonium; metals, such as $Cu^+$, $K^+$, $Li^+$, and $Na^+$; alkyl metal complexes, such as $CH_3Hg^+$; metal oxides, such as $NpO_2^+$, $PaO_2^+$, and $PuO_2^+$; metal hydroxides, such as $CaOH^+$, $FeOH^+$, $BaOH^+$, $Al(OH)_2^+$, $Ir(OH)_2^+$, $Pb(OH)_3^+$, and $Nb(OH)_4^+$; cationic metal halides, such as $Al(X)_2^+$, $CaX^+$, $Cr(X)_2^+$, and $Pb(X)_3^+$, where X is fluoride, chloride, bromide, or iodide; and mixtures thereof.

Preferred monovalent anions include, but are not limited to halides; alkoxides; hydroxides; deprotonated acids, such as $CN^-$, $SCN^-$, $OCN^-$, $NO_3^-$, $NO_2^-$, $H_2PO_4^-$, and $HSO_4^-$; and anionic metal halides, such a $Al(X)_4^-$, $Ba(X)_3^-$, and $Fe(X)_3^-$, where X is fluoride, chloride, bromide, or iodide; and mixtures thereof.

Examples of multivalent cations are ionized alkaline earth metals, such as calcium, magnesium, beryllium, strontium, barium, and radium. Examples of multivalent anions include multi-atom ions, such as sulfate, hydrogen phosphate, and oxalate. Other examples of multivalent ions include titanium (III), chromium(III), manganese(III), iron(III), cobalt(III) iridium(IV), and phosphate. Especially preferred multivalent ions include alkaline earth metal ions, Group IIIA metal ions, Group IVA metal ions, $Al^{3+}$, $Sn^{4+}$, $Pb^{4+}$, $Ti^{3+}$, $Cr^{3+}$, $Mn^{3+}$, $Fe^{3+}$, $Ni^{2+}$, $Cu^{2+}$, $Co^{3+}$, $Ir^{3+}$, $CO_3^{2-}$, $PO_4^{3-}$, $SO_3^{2-}$, $S^{2-}$, $Te^{2-}$, $Se^{2-}$, $N^{3-}$, $P^{3-}$, $O_2^{2-}$, and mixtures thereof.

Preferred multivalent cations include, but are not limited to metals capable of carrying a +2 or higher charge, such as $Ba^{2+}$, $Ca^{2+}$, $Cd^{2+}$, $Co^{2+}$, $Cu^{2+}$, $Fe^{2+}$, $Hg^{2+}$, $Mg^{2+}$, $Mn^{2+}$, $Ni^{2+}$, $Pb^{2+}$, $Zn^{2+}$, $Pd^{2+}$, $Sn^{2+}$, $Sr^{2+}$, $V^{2+}$, $Pb^{4+}$, $Pu^{4+}$, $Sn^{4+}$, $Th^{4+}$, $U^{4+}$, and $Zr^{4+}$; divalent and higher metal oxides, such as $UO_2^{2+}$ and $VO^{2+}$; divalent and higher metal hydroxides, such as $AlOH^{2+}$, $TiOH^{2+}$, $Ti(OH)_2^{2+}$, and $MnOH^{2+}$; divalent and higher cationic metal halides, such as $AlX^{2+}$, $Pb(X)_2^{2+}$, $Ti(X)_2^{2+}$, and $MnX^{2+}$, where X is fluoride, chloride, bromide, or iodide; and mixtures thereof.

Preferred multivalent anions include, but are not limited to elements and multi-atom complexes capable of carrying a $^2-$ or lower charge, such as $Te^{2-}$, $S^-$, $HAsO_4^{2-}$, $MnO_4^{2-}$, $Ca(OH)_4^{2-}$, $Mg(OH)_4^{2-}$, $Hg(OH)_4^{2-}$, $V_2O_7^{4-}$, and $Mn(OH)_4^{2-}$; halide complexes capable of carrying a $^-2$ or lower charge, such as $Co(X)_4^{2-}$, $Cu(X)_4^{2-}$, $Fe(X)_4^{2-}$, $Th(X)_6^{2-}$, and $Ti(X)_6^{2-}$, where X is fluoride, chloride, bromide, or iodide; and mixtures thereof.

The molarity of ions solvated in a colloidal suspension is determined by analyzing a sample of the carrier liquid, which contains the ions, by Inductively Coupled Plasma (ICP) analysis. The carrier liquid may be initially separated from the suspended particles, by for example, centrifugation. By this method, the quantity and atomic identity of the solvated ions is determined. Thus, the molarity of ions in the carrier liquid may be determined and their oxidation states may be implied from their identities.

High ionic strength colloidal suspensions may be initially created (such as through the addition of electrolytes that dissociate to form ions in the carrier liquid), or may form over time through dissolution of the suspended particles of an initially lower ionic strength suspension. One way that the ionic strength of a suspension increases over time is when some of the suspended colloidal particles, or the ions on their surface, are solvated into the carrier liquid. This increased solvation over time, or "dissolution," can increase the ionic strength of a colloidal suspension by increasing the solvated ion concentration in the suspension. Colloidal suspensions containing small particles, such as particles having effective diameters in the nanometer range, are especially susceptible to dissolution. By stabilizing colloidal suspensions that increase in ionic strength over time, the preferred embodiments beneficially increase the long term stability, or shelf life, of the suspension.

Determination of Critical Concentration

To achieve the desired stabilization of a colloidal suspension containing ceramic precursor, bioactive agents, or other particles, a critical concentration may be determined. By adding increasing amounts of comb polymers with ionizable and nonionizable side-chains to a suspension and measuring the viscosity, one can determine the optimal (lowest) amount of a specific comb polymer required to attain the desired viscosity reduction (stability). Critical concentration is defined as the lowest amount of comb polymer required to attain stability for a colloidal suspension.

Figure 8:
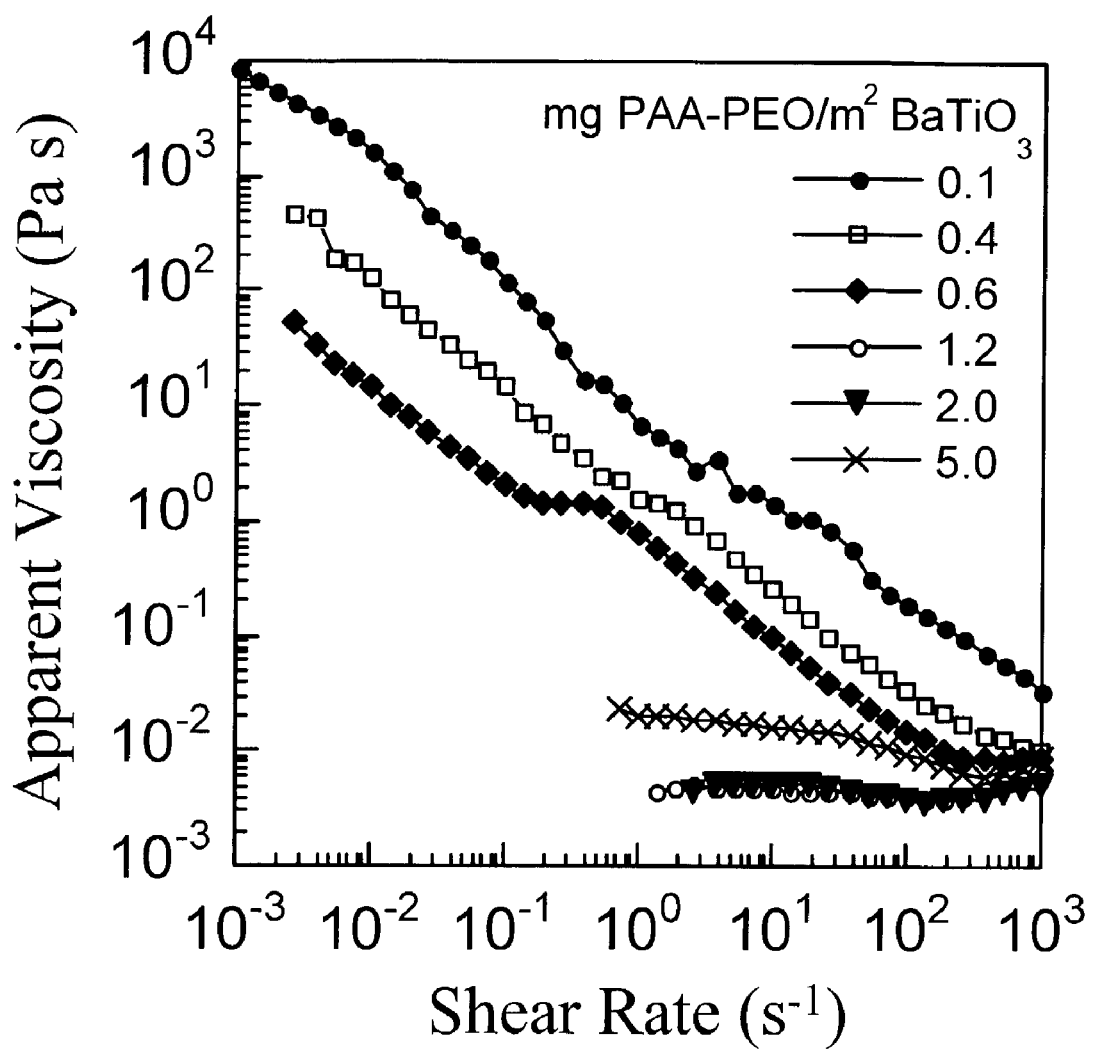
FIG. 8 is a plot of apparent viscosity as a function of shear rate for $BaTiO_3$ suspensions with varying PAA-PEO(1 K) concentration.
Figure 9:
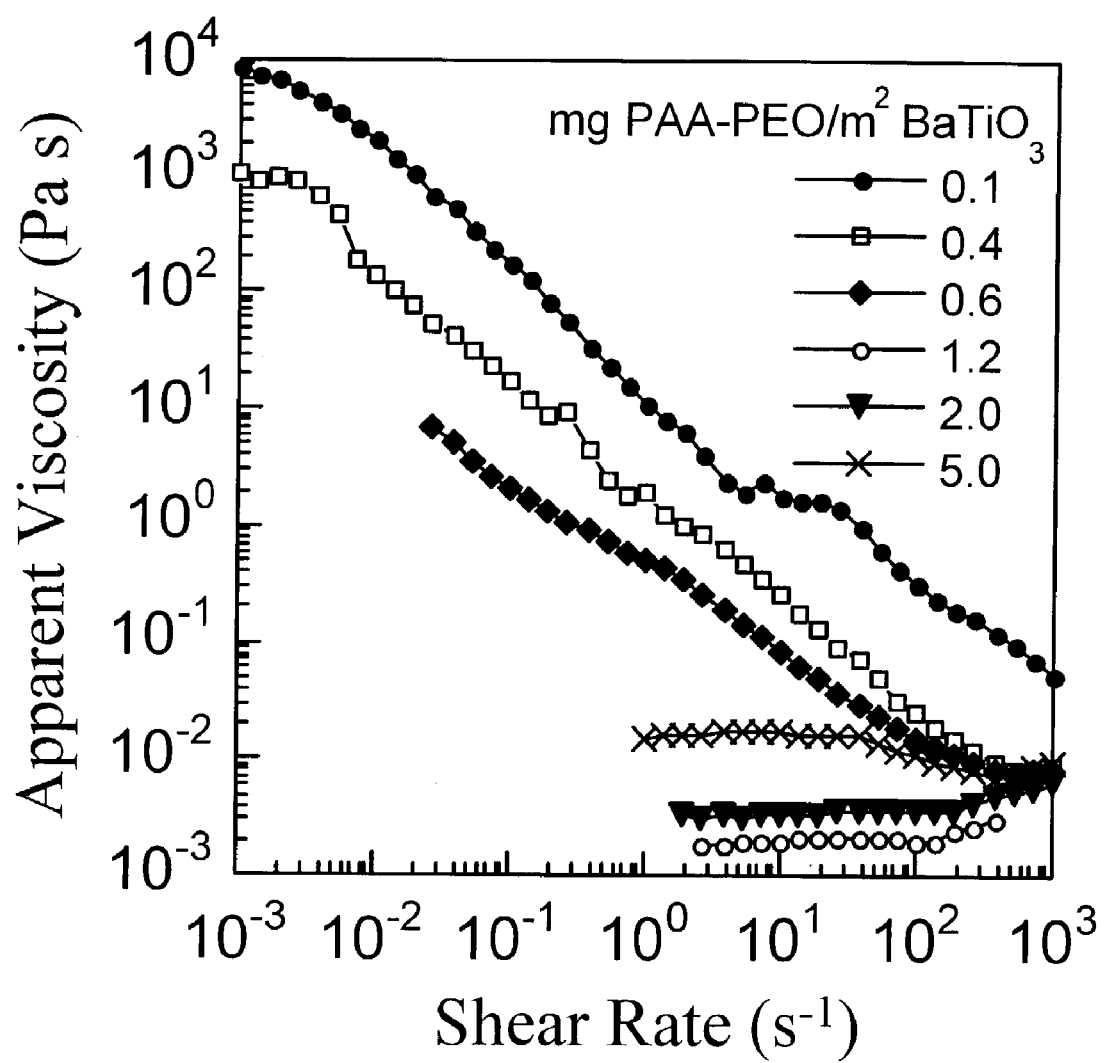
FIG. 9 is a plot of apparent viscosity as a function of shear rate for $BaTiO_3$ suspensions with varying PAA-PEO(2K) concentration.

As shown in the viscosity plots of FIGS. 8 and 9, for a colloidal suspension containing $BaTiO_3$ particles, the critical concentration of PAA-PEO is at the 1.2 mg level per $m^2$ of $BaTiO_3$ surface. Neither greater (2.0 mg), nor lesser (0.6 mg), amounts of the comb polymer dispersant lower viscosity as well.

The comb polymers may be used in most particulate suspensions. Examples include suspensions used to form ceramics, ceramic substrates for electronic packaging, capacitors, mesoporous structures, photonics, inks, paints, coatings, cosmetics, food products, drilling muds, dyestuffs, foams, agricultural chemicals, and pharmaceuticals. Additionally, colloidal suspensions containing metallic particles may be used as cleaning abrasives, catalysts, powder metallurgy precursors, electrode precursors, dental amalgams, lubricants, magnetic materials, food preservatives, and disinfectants as well as in pharmaceutical compositions and for biomedical applications.

The present embodiments are especially useful in the area of ceramics fabrication where it is desirable to produce ceramic precursor colloidal suspensions containing multivalent ions and/or high concentrations of monovalent ions. As the concentration of particles is increased in the suspension, their tendency to aggregate or flocculate increases. The use of effective dispersants to reduce viscosity allows for preparation of high solids-content ceramic precursor suspensions.

If appropriate ceramic precursor particles are chosen, the resultant colloidal suspension may be solidified to directly form solid structures, such as ceramic substrates for electronic devices, or to form electronic materials, such as would be suitable for use in capacitors. The colloidal suspensions may be solidified using heat (sintering or firing in a kiln, for example) or other methods which bring about the desired solidification. In the case of some devices, only partial solidification may be desired. Depending on the device or substrate desired, the particles may be allowed to partially flocculate, thus becoming gel-like in nature, or even precipitate, prior to solidification.

Many pharmaceutical uses also exist for a colloidal suspension having adjustable viscosity. In these applications, bio-compatible comb polymers, such as those with polylactic acid backbones, are preferred. Bio-compatible means the comb polymer is not toxic to living systems at the quantity used. Because the amount of colloidal stabilization provided by a specific type and quantity of bio-compatible comb polymer is pH dependent, pH changes that occur when the colloidal suspension is administered orally, subcutaneously, or intravenously can be used to alter the phase of the comb polymer stabilized colloid. One such use, for example, is to alter the viscosity of injectable pharmaceutical compositions containing one or more bioactive agents.

It can be advantageous to have a very low viscosity drug composition that can pass through a very fine needle into the body, but yet have the drug composition stay localized in the tissue at the region of injection. This localized region is characterized by its phase separation from the physiological fluid and its decreased fluidity relative to the original suspension. By adding a comb polymer dispersant to the colloidal drug composition that lowers viscosity at the pH of the delivery suspension, but not at physiological pH, a drug composition can exist at a relatively low viscosity in the syringe, but at a relatively higher viscosity in the body. In this fashion, the pharmaceutical is easily delivered to a specific location.

EXAMPLES

Example 1

Preparation of a Comb Polymer Stabilized Colloidal Suspension Containing Multivalent Ions.

Barium titanate ($BaTiO_3$) nanoparticles (BT-16 K-Plus, Cabot Co., Boyertown, Pa.) with an average effective diameter of 60 nm, a specific surface area of 16.4 $m^2/g$, and a density of 5.88 $g/cm^3$ served as the ceramic precursor powder in this study.

Polyacrylic acid (PAA) having an average molecular weight of 5000 g/mol is obtainable from Polyscience Inc., Warrington, Pa. Comb polymers having various backbones, including PAA, polymethacrylic acid, and polystyrene, for example, and various ratios of ionizable to nonionizable side chains may be obtained from many sources. These include Takemoto Oil & Fat Co., Ltd., Japan (Chupol series: carboxylated acrylic esters); Polymer Source, Inc., Dorval, Quebec, Canada (PM backbones with PEO caps); Silkroad C&T, Korea (PEMA-200N: polycarboxylic ethers); Axim Italcementi Group, Cambridge, Ontario (Catexol Superflux 2000 PC: polycarboxylated polymers); and Grace Construction Products, Cambridge, MA (ADVA Flow: carboxylated polyether). Comb polymers having PM backbone with PEO caps of an average molecular weight of 1000 g/mol (denoted as PM-PEO(1 K)) or 2000 g/mol (denoted as PAA-PEO (2K)), respectively, served as the comb polymer dispersants for Examples 1 and 2.

$BaTiO_3$ suspensions were prepared by dispersing an appropriate amount of this powder in an aqueous dispersant solution. The solution was premixed by adding an appropriate dispersant amount to deionized water followed by magnetic stirring for 0.5 h. Upon adding $BaTiO_3$ powder, the suspension was ultrasonicated (F550 Sonic Dismembrator, Fisher Scientific, Kosmonautu 324, CZ-53009 Pardubice, CZECH REPUBLIC) for 5 min using a 1 s on/off pulse sequence. The suspension pH was adjusted to 9 using 0.1 M $HNO_3$ and 0.1 M $NH_4OH$ solutions. The suspensions were then magnetically stirred for 24 h.

Representative aliquots of these suspensions were dosed with 0.5 M, 0.1 M, 0.01 M, or 0.001 M stock solutions of $BaCl_2$ as a source of multivalent $^+2$ and monovalent $^-1$ counterions. These electrolytic salt solutions were prepared by dissolving $BaCl_2 \cdot 2H_2O$ salt (Fisher Chemicals, Fair Lawn, N.J.) in deionized water.

Figure 5:
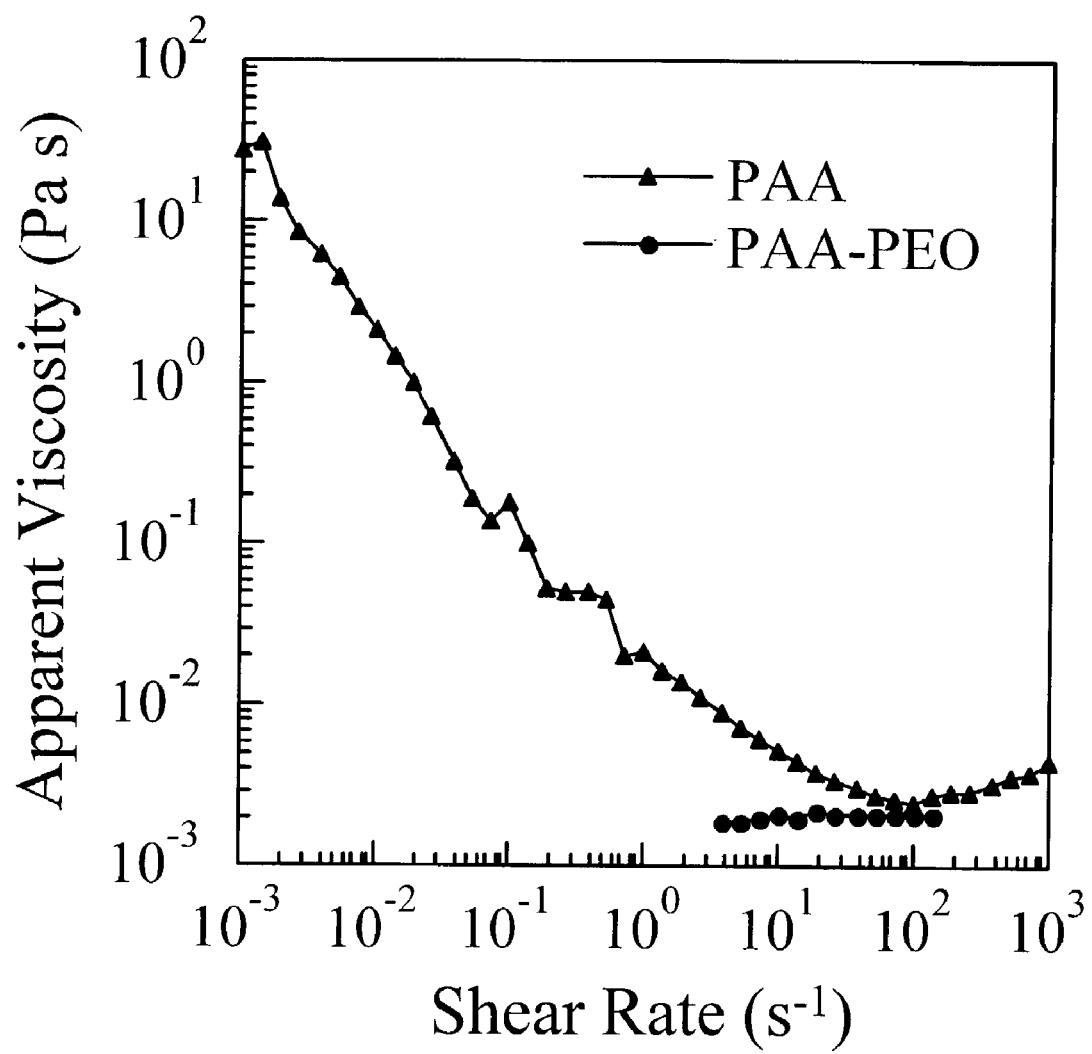
FIG. 5 is a plot showing the significantly reduced viscosity of a colloidal suspension when PAA-PEO versus PAA dispersant is used in the presence of multivalent cations.

As can be seen from FIG. 5, the $BaTiO_3$-PAA based system exhibited large viscosities upon dosing with only 0.001 M $BaCl_2$ salt, whereas the $BaTiO_3$-PAA-PEO comb-polymer based system retained low viscosities upon dosing with 0.001 M $BaCl_2$ salt.

Example 2

Preparation of a Comb Polymer Stabilized Colloidal Suspension Containing a High Concentration of Monovalent Ions.

Colloidal ceramic precursor suspensions containing $BaTiO_3$ were prepared as in Example 1. Representative aliquots of these suspensions were dosed with 0.1 M, 0.5 M, 1.0 M, or 2.0 M stock solutions of KCl as a source of monovalent $^+1$ and $^-1$ counterions. These electrolytic salt solutions were prepared by dissolving KCl (Fisher Chemicals, Fair Lawn, N.J.) in deionized water.

Figure 6:
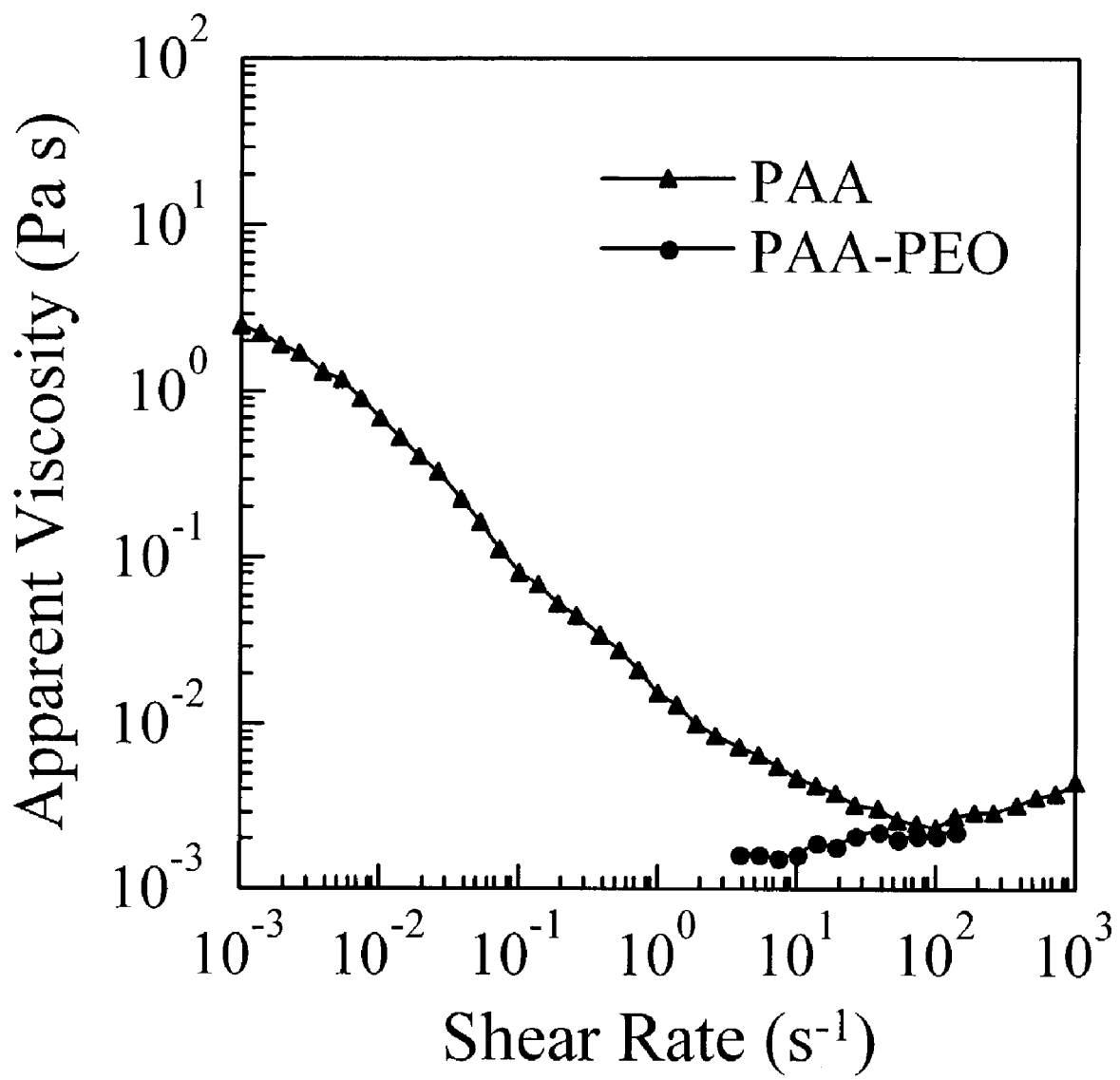
FIG. 6 is a plot showing the significantly reduced viscosity of a colloidal suspension when PAA-PEO versus PAA dispersant is used in the presence of a high concentration of monovalent cations.
Figure 7:
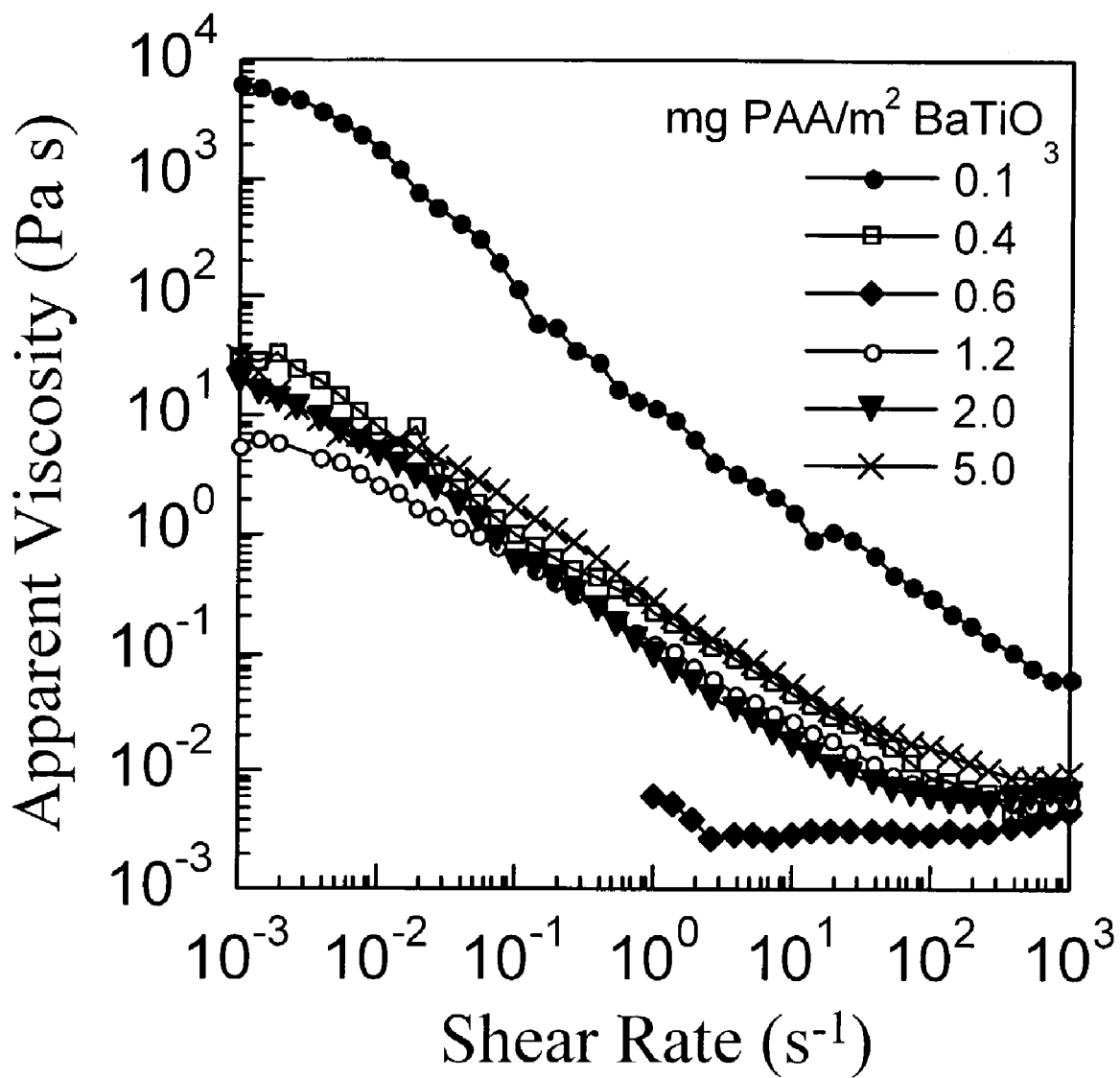
FIG. 7 is a plot of apparent viscosity as a function of shear rate for $BaTiO_3$ suspensions with varying PAA concentration.

As can be seen from FIG. 6 the $BaTiO_3$-PAA system exhibited large viscosities upon dosing with 0.003 M KCl salt, whereas the $BaTiO_3$PAA-PEO comb-polymer based system retained low viscosities upon dosing with 0.003 M KCl salt.

Prophetic Example 1

Preparation of a Pharmaceutical Composition Stabilized with a Bio-Compatible Comb Polymer.

A pharmaceutical composition including a chemotherapeutic drug and a biodegradable polymer is prepared and formed into particles. Suspensions of the particles are prepared by dispersing the particles in an aqueous solution of comb polymer dispersant.

The comb polymer dispersant consists of a poly(lactic acid) backbone with PEO caps.

An aqueous solution of the dispersant is premixed by adding the dispersant to deionized water followed by magnetic stirring for 0.5 h. The pharmaceutical composition particles are added to the aqueous dispersant solution. Upon adding the pharmaceutical particles, the suspension is ultrasonicated (F550 Sonic Dismembrator, Fisher Scientific, Kosmonautu 324, CZ-53009 Pardubice, CZECH REPUBLIC) for 5 min using a 1 s on/off pulse sequence. The suspension pH is adjusted to 7.2 to simulate biological conditions.

Prophetic Example 2

A Ceramic Substrate is Prepared from a Colloidal Suspension Containing Ceramic Precursor Particles Stabilized with Comb Polymers.

Fifty mL of a concentrated, well-dispersed aqueous alumina-comb polymer suspension (33.3% solids by volume, 1 mg comb polymer/$m^2$ of alumina) is prepared by the following procedure. First, 0.70 g of the comb polymer and 24.3 g of deionized water are combined and mixed for 10 min to form a solution. Then, the solution is combined with 66.167 g of the as-received alumina precursor (AKP 50, Sumitomo). The resultant mixture is ultrasonicated with 1 sec on/off pulses for 5 min, followed by 12 h of stirring to form a dispersed, colloidal alumina suspension. A pH of 9 is maintained throughout the suspension preparation procedure.

About nine grams of an acrylic latex binder (16.7% solids by volume) is added to the aqueous alumina-comb polymer suspension and mixed for 2 h. The ceramic substrate is then formed with a tape casting procedure, as described by Reed, pp. 525–541 in *Principles of Ceramic Processing*, 2nd ed, John Wiley & Sons, Inc. (1995), incorporated by reference in its entirety, except that in the event of any inconsistent disclosure or definition from the present application, the disclosure or definition herein shall be deemed to prevail.

After casting, the tape is sectioned to the appropriate dimensions and dried under controlled-humidity conditions. The binder is removed by heating the green ceramic substrate at 10° C./min to 250° C., 1° C./min to 300° C., 1 h dwell at 300° C., 1° C./min to 600° C., and finally, a 1 h dwell at 600° C. The substrate is then sintered in air at 1600° C. for 1 h.

As any person skilled in the art of colloidal suspensions will recognize from the previous description, figures, and examples that modifications and changes can be made to the preferred embodiments of the invention without departing from the scope of the invention defined by the following claims.

What is claimed:

1. A colloidal suspension comprising:
   particles selected from the group consisting of metals, ceramic precursors, semiconductors, polymers, biodegradable polymers, bioactive agents, and mixtures thereof;
   a comb polymer; and
   multivalent ions,
   wherein said suspension comprises said multivalent ions at a concentration of at least 0.001 M,
   the particles have an average effective diameter from 1 nanometer to 3 microns,
   the comb polymer comprises a polymer having ionizable and nonionizable side-chains, and
   a ratio of the ionizable to the nonionizable side-chains is from 20:1 to 1:1.

2. The colloidal suspension of claim 1, wherein the particles are stabilized against flocculation.

3. The colloidal suspension of claim 1, wherein the colloidal suspension comprises water.

4. The colloidal suspension of claim 3, wherein the colloidal suspension further comprises a liquid less polar than water.

5. The colloidal suspension of claim 4, wherein said liquid less polar than water is selected from the group consisting of alcohol, methanol, propanol, ethanol, t-butanol, N,N-dimethylformamide, dimethyl sulfoxide, acetone, acetonitrile, acetic acid, hexamethylphosphoric triamide, tetrahydrofuran, N, N-d imethylacetamide, N-methyl-2-pyrrolidone, tetramethyl urea, glycerol, ethylene g lycol, and mixtures thereof.

6. The colloidal suspension of claim 1, wherein said particles have an average effective diameter from 20 nanometers to 3 microns.

7. The colloidal suspension of claim 1, wherein said particles are selected from the group consisting of tool steels, molybdenum, nickel, gold, silver, platinum, titanium-aluminum-vanadium alloys, tungsten, aluminum, alloys thereof, and mixtures thereof.

8. The colloidal suspension of claim 1, wherein said particles are selected from the group consisting of hydroxyapatite, titanium oxide, lead zirconate, titanate, alumina, silica, zirconia, silicon nitride, silicon carbide, and mixtures thereof.

9. The colloidal suspension of claim 1, wherein said particles are selected from the group consisting of acrylic latexes, poly(ethyl methacrylate), cellulose polystyrene, poly(methyl methacrylate), poly(lactic acids), natural rubber, polyethylene, poly(vinyl chloride), and mixtures thereof.

10. The colloidal suspension of claim 1, wherein said particles comprise a bioactive agent selected from the group consisting of drugs, proteins, enzymes, polynucleotides, lipoproteins, liposomes, polypeptides, chemotherapeutic agents, hormones, polysaccharides, steroids, analgesics, local anesthetics, antibiotic agents, anti-inflammatory corticosteroids, and mixtures thereof.

11. The colloidal suspension of claim 1, wherein the ionizable side-chains comprise a carboxylic acid moiety and the nonionizable side-chains comprise a polyethylene oxide moiety.

12. The colloidal suspension of claim 1, wherein the comb polymer has a backbone having an average molecular weight from 1,000 to 15,000.

13. The colloidal suspension of claim 1, wherein said multivalent ions are selected from the group consisting of alkaline earth metal ions, Group IIIA metal ions, Group IVA metal ions, $Al^{3+}$, $Sn^{4+}$, $Pb^{4+}$, $Ti^{3+}$, $Cr^{3+}$, $Mn^{3+}$, $Fe^{3+}$, $Ni^{2+}$, $Cu^{2+}$, $Co^{3+}$, $Ir^{3+}$, $CO_3^{2-}$, $PO_4^{3-}$, $SO_3^{2-}$, $S^{2-}$, $Te^{2-}$, $Se^{2-}$, $N^{3-}$, $P^{3-}$, $O^{2-}$, and mixtures thereof.

14. The colloidal suspension of claim 1, wherein said ion concentration is at least 0.01 M.

15. The colloidal suspension of claim 1, wherein said ion concentration is at least 0.1 M.

16. A colloidal suspension comprising:
particles selected from the group consisting of metals, ceramic precursors, semiconductors, polymers, biodegradable polymers, bioactive agents, and mixtures thereof;
a comb polymer; and
monovalent ions,
wherein said suspension comprises said monovalent ions at a concentration of at least 0.1 M,
the particles have an average effective diameter of from 1 nanometer to 3 microns,
the comb polymer comprises a polymer having ionizable and non-ionizable side chains, and
a ratio of the ionizable to non-ionizable side chains is from 20:1 to 1:1.

17. The colloidal suspension of claim 16, wherein the particles are stabilized against flocculation.

18. The colloidal suspension of claim 16, wherein the colloidal suspension comprises water.

19. The colloidal suspension of claim 18, wherein the colloidal suspension further comprises a liquid less polar than water.

20. The colloidal suspension of claim 19, wherein said liquid less polar than water is selected from the group consisting of alcohol, methanol, propanol, ethanol, t-butanol, N,N-dimethylformamide, dimethyl sulfoxide, acetone, acetonitrile, acetic acid, hexamethylphosphoric triamide, tetrahydrofuran, N,N-dimethylacetamide, N-methyl-2-pyrrolidone, tetramethyl urea, glycerol, ethylene glycol, and mixtures thereof.

21. The colloidal suspension of claim 16, wherein said particles have an average effective diameter from 20 nanometers to 3 microns.

22. The colloidal suspension of claim 16, wherein said particles are selected from the group consisting of tool steels, molybdenum, nickel, gold, silver, platinum, titanium-aluminum-vanadium alloys, tungsten, aluminum, alloys thereof, and mixtures thereof.

23. The colloidal suspension of claim 16, wherein said particles are selected from the group consisting of hydroxyapatite, titanium oxide, lead zirconate, titanate, alumina, silica, zirconia, silicon nitride, silicon carbide, and mixtures thereof.

24. The colloidal suspension of claim 16, wherein said particles are selected from the group consisting of acrylic latexes, poly(ethyl methacrylate), cellulose polystyrene, poly(methyl methacrylate), poly(lactic acids), natural rubber, polyethylene, poly(vinyl chloride), and mixtures thereof.

25. The colloidal suspension of claim 16, wherein said particles comprise a bioactive agent selected from the group consisting of drugs, proteins, enzymes, polynucleotides, lipoproteins, polypeptides, chemotherapeutic agents, hormones, polysaccharides, steroids, analgesics, local anesthetics, antibiotic agents, anti-inflammatory corticosteroids, and mixtures thereof.

26. The colloidal suspension of claim 16, wherein the ionizable side-chains comprise a carboxylic acid moiety and the nonionizable side-chains comprise a polyethylene oxide moiety.

27. The colloidal suspension of claim 16, wherein the comb polymer has a backbone having an average molecular weight from 1,000 to 15,000.

28. The colloidal suspension of claim 16, wherein said monovalent ions are selected from the group consisting of halides, ionized alkali earth metals, $NH_4^+$; $NO_3^-$, $ClO_3^-$, $IO_3^-$, and mixtures thereof.

29. The colloidal suspension of claim 16, wherein said ion concentration is at least 0.5 M.

30. The colloidal suspension of claim 16, wherein said ion concentration is at least 1.0 M.

31. A colloidal suspension comprising:
particles selected from the group consisting of hydroxyapatite, titanium oxide, lead zirconate, titanate, alumina, silica, zirconia, silicon nitride, silicon carbide, and mixtures thereof;
a comb polymer; and
multivalent ions,
wherein said suspension comprises said multivalent ions at a concentration of at least 0.001 M,
the particles have an average effective diameter from 1 nanometer to 3 microns,
the comb polymer comprises a polymer having ionizable and nonionizable side-chains, and
a ratio of the ionizable to the nonionizable side-chains is from 20:1 to 1:1.

32. A colloidal suspension comprising:
particles selected from the group consisting of hydroxyapatite, titanium oxide, lead zirconate, titanate, alumina, silica, zirconia, silicon nitride, silicon carbide, and mixtures thereof;
a comb polymer; and
monovalent ions,
wherein said suspension comprises said monovalent ions at a concentration of at least 0.1 M,
the particles have an average effective diameter of from 1 nanometer to 3 microns,
the comb polymer comprises a polymer having ionizable and non-ionizable side chains, and
a ratio of the ionizable to non-ionizable side chains is from 20:1 to 1:1.

33. In a colloidal suspension including ceramic precursor particles, multivalent ions at a concentration of at least 0.001 M, a carrier liquid, and a dispersant, the improvement comprising at least one comb polymer as the dispersant,
wherein the particles have an average effective diameter from 1 nanometer to 3 microns.
the comb polymer comprises a polymer having ionizable and nonionizable side-chains, and
a ratio of the ionizable to the nonionizable side-chains is from 20:1 to 1:1.

34. In a colloidal suspension including ceramic precursor particles having an average effective diameter of from 1 nanometer to 3 microns, monovalent ions at a concentration of at least 0.1 M, a carrier liquid, and a dispersant, the improvement comprising at least one comb polymer as the dispersant, wherein the comb polymer comprises a polymer having ionizable and non-ionizable side chains in a ratio of ionizable to non-ionizable side chains of from 20:1 to 1:1.

35. The colloidal suspension of claim 1,
wherein said suspension is a pharmaceutical composition,
said particles comprise a bioactive agent, and
said comb polymer comprises ionizable and nonionizable side-chains.

36. The pharmaceutical composition of claim 35, wherein said comb polymer is water-soluble.

37. The pharmaceutical composition of claim 35, wherein said comb polymer is bio-compatible.

38. The colloidal suspension of claim 16,
wherein said suspension is a pharmaceutical composition,
said particles comprise a bioactive agent, and
said comb polymer comprises ionizable and nonionizable side-chains.

39. The pharmaceutical composition of claim 38, wherein said comb polymer is water-soluble.

40. The pharmaceutical composition of claim 38, wherein said comb polymer is bio-compatible.

* * * * *

UNITED STATES PATENT AND TRADEMARK OFFICE
CERTIFICATE OF CORRECTION

PATENT NO. : 7,053,125 B2 Page 1 of 1
APPLICATION NO. : 10/336636
DATED : May 30, 2006
INVENTOR(S) : Jennifer A. Lewis et al.

It is certified that error appears in the above-identified patent and that said Letters Patent is hereby corrected as shown below:

In the Claims:

Col. 17, line 1, please delete "N-d imethylacetamide" and insert --N-dimethylacetamide--.
Col. 17, line 2, please delete "g lycol" and insert --glycol--.

Signed and Sealed this

Sixth Day of March, 2007

JON W. DUDAS
*Director of the United States Patent and Trademark Office*